US010065739B2

(12) United States Patent
Duesterhoft et al.

(10) Patent No.: US 10,065,739 B2
(45) Date of Patent: Sep. 4, 2018

(54) SYSTEMS AND METHODS FOR DRONE TRACKING OF AIRBORNE MATERIALS

(71) Applicant: Elwha LLC, Bellevue, WA (US)

(72) Inventors: Paul Duesterhoft, Grapevine, TX (US); William David Duncan, Mill Creek, WA (US); Roderick A. Hyde, Redmond, WA (US); Jordin T. Kare, San Jose, CA (US); Eric C. Leuthardt, St. Louis, MO (US); Tony S. Pan, Bellevue, WA (US); Lowell L. Wood, Jr., Bellevue, WA (US)

(73) Assignee: Elwha LLC, Bellevue, WA (US)

( * ) Notice: Subject to any disclaimer, the term of this patent is extended or adjusted under 35 U.S.C. 154(b) by 133 days.

(21) Appl. No.: 14/745,992

(22) Filed: Jun. 22, 2015

(65) Prior Publication Data

US 2016/0370263 A1 Dec. 22, 2016

(51) Int. Cl.

| | |
|---|---|
| ***B64D 1/00*** | (2006.01) |
| ***B64C 39/02*** | (2006.01) |
| ***G01N 33/00*** | (2006.01) |
| ***B64D 1/02*** | (2006.01) |
| ***B64D 1/16*** | (2006.01) |
| *B64B 1/00* | (2006.01) |

(52) U.S. Cl.

CPC .............. *B64D 1/00* (2013.01); *B64C 39/024* (2013.01); *B64D 1/02* (2013.01); *B64D 1/16* (2013.01); *G01N 33/0004* (2013.01); *B64B 1/00* (2013.01); *B64C 2201/027* (2013.01); *B64C 2201/12* (2013.01); *B64C 2201/146* (2013.01)

(58) Field of Classification Search

CPC ..... B64C 39/024; B64C 2201/12; B64D 1/00; G01N 1/2273

See application file for complete search history.

(56) References Cited

U.S. PATENT DOCUMENTS

| | | | |
|---|---|---|---|
| 3,077,779 | A | 2/1963 | Froehlich et al. |
| 4,226,115 | A | 10/1980 | Williams et al. |
| 4,995,572 | A | 2/1991 | Piasecki |
| 5,340,025 | A | 8/1994 | Pearce |

(Continued)

OTHER PUBLICATIONS

Straw, Joseph, "FAA says New York, five other states chosen to host drone test sites," New York Daily News, http://www.nydailynews.com/news/politics/6-states-chosen-drone-test-sites-article-1.1561480, Dec. 30, 2013, date visited Jun. 23, 2015.

(Continued)

*Primary Examiner* — Philip J Bonzell

(57) ABSTRACT

An unmanned aerial vehicle may be used to monitor and/or track airborne material in a plume. The unmanned aerial vehicle may be configured to eject a tracer material into the plume. The unmanned aerial vehicle may include a sensor for detecting the tracer material. The sensor may detect the position, the velocity, the concentration, amount reacted, etc. of the tracer material. The unmanned aerial vehicle and/or a remote vehicle or facility may include an electromagnetic radiation emitter to irradiate the tracer material. The sensor may measure the interactions of the electromagnetic radiation with the tracer material. The unmanned aerial vehicle and/or a remote system may determine characteristics of the plume and/or a substance of interest based on measurements by the sensor.

41 Claims, 11 Drawing Sheets

(56) References Cited

U.S. PATENT DOCUMENTS

| | | | | |
|---|---|---|---|---|
| 6,066,295 | A * | 5/2000 | Bernstein | G01V 8/00 250/340 |
| 7,073,748 | B2 | 7/2006 | Maurer et al. | |
| 7,319,039 | B2 * | 1/2008 | Sullivan | G01N 21/6428 250/458.1 |
| 7,341,224 | B1 | 3/2008 | Osann, Jr. | |
| 7,679,563 | B2 | 3/2010 | Werner et al. | |
| 7,684,043 | B2 * | 3/2010 | Dorvee | G01N 21/39 356/437 |
| 7,811,520 | B2 | 10/2010 | Bernhardt | |
| 7,840,380 | B2 * | 11/2010 | Bernhardt | G01J 3/42 250/494.1 |
| 7,985,590 | B2 | 7/2011 | McNeil | |
| 8,153,435 | B1 | 4/2012 | Fraser | |
| 8,501,481 | B1 | 8/2013 | Fraser | |
| 8,820,672 | B2 * | 9/2014 | Erben | B64C 39/024 244/1 R |
| 9,255,775 | B1 | 2/2016 | Rubin | |
| 9,481,460 | B1 | 11/2016 | Kozloski et al. | |
| 2003/0066932 | A1 | 4/2003 | Carroll | |
| 2004/0189976 | A1 | 9/2004 | Burns et al. | |
| 2005/0080586 | A1 | 4/2005 | Kanevsky et al. | |
| 2006/0262318 | A1 * | 11/2006 | Sullivan | G01N 21/6428 356/484 |
| 2008/0204752 | A1 * | 8/2008 | Dorvee | G01N 21/39 356/402 |
| 2008/0224947 | A1 | 9/2008 | Werner et al. | |
| 2009/0222207 | A1 | 9/2009 | Bernhardt | |
| 2010/0285490 | A1 | 11/2010 | Dees et al. | |
| 2010/0304491 | A1 | 12/2010 | McNeil | |
| 2011/0251800 | A1 | 10/2011 | Wilkins | |
| 2012/0268308 | A1 | 10/2012 | Tuttle | |
| 2013/0176570 | A1 | 7/2013 | Beck et al. | |
| 2013/0208262 | A1 | 8/2013 | Andreussi | |
| 2013/0278427 | A1 * | 10/2013 | Setton | G08B 21/12 340/584 |
| 2014/0011286 | A1 | 1/2014 | Potyrailo | |
| 2014/0057276 | A1 | 2/2014 | Farquar et al. | |
| 2016/0288904 | A1 | 10/2016 | Tanielian | |
| 2016/0368604 | A1 * | 12/2016 | Duesterhoft | B64D 1/02 |

OTHER PUBLICATIONS

Environmental Protection Agency, “Air Quality Plume Detection and Monitoring Using UAVs and Unmanned Rotorcraft,” www.epa.gov/airnow/2010conference/naqc/forecasting/kosmatka_final.pdf Date visited Jun. 23, 2015.

Federal Aviation Administration, “Minimum Safe Altitudes,” Code of Federal Regulations Sec. 91.119 http://rgl.faa.gov/regulatory_and_guidance_library/rgfar.nsf/b4a0cab3e513bb58852566c70067018f/91693c93525de33e862576c100763e31!OpenDocument date visited Jun. 23, 2015.

* cited by examiner

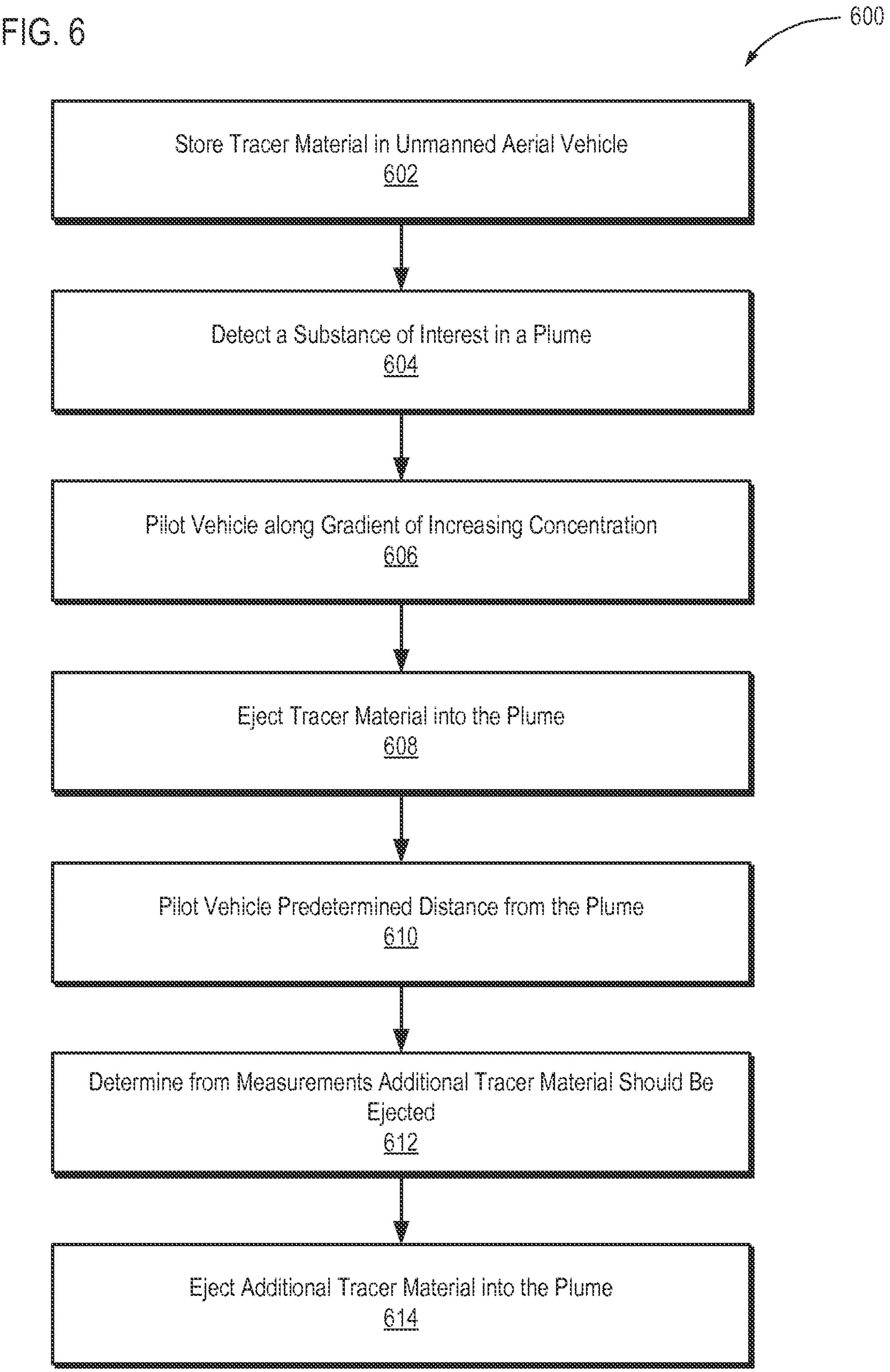

FIG. 6

```
┌─────────────────────────────────────────┐
│ Store Tracer Material in Unmanned Aerial Vehicle │
│                   602                   │
└─────────────────────────────────────────┘
                    │
                    ▼
┌─────────────────────────────────────────┐
│     Detect a Substance of Interest in a Plume     │
│                   604                   │
└─────────────────────────────────────────┘
                    │
                    ▼
┌─────────────────────────────────────────┐
│  Pilot Vehicle along Gradient of Increasing Concentration  │
│                   606                   │
└─────────────────────────────────────────┘
                    │
                    ▼
┌─────────────────────────────────────────┐
│       Eject Tracer Material into the Plume       │
│                   608                   │
└─────────────────────────────────────────┘
                    │
                    ▼
┌─────────────────────────────────────────┐
│   Pilot Vehicle Predetermined Distance from the Plume   │
│                   610                   │
└─────────────────────────────────────────┘
                    │
                    ▼
┌─────────────────────────────────────────┐
│ Determine from Measurements Additional Tracer Material Should Be Ejected │
│                   612                   │
└─────────────────────────────────────────┘
                    │
                    ▼
┌─────────────────────────────────────────┐
│    Eject Additional Tracer Material into the Plume    │
│                   614                   │
└─────────────────────────────────────────┘
```

600

SYSTEMS AND METHODS FOR DRONE TRACKING OF AIRBORNE MATERIALS

If an Application Data Sheet ("ADS") has been filed on the filing date of this application, it is incorporated by reference herein. Any applications claimed on the ADS for priority under 35 U.S.C. §§ 119, 120, 121, or 365(c), and any and all parent, grandparent, great-grandparent, etc., applications of such applications, are also incorporated by reference, including any priority claims made in those applications and any material incorporated by reference, to the extent such subject matter is not inconsistent herewith.

CROSS-REFERENCE TO RELATED APPLICATIONS

The present application claims the benefit of the earliest available effective filing date(s) from the following listed application(s) (the "Priority Applications"), if any, listed below (e.g., claims earliest available priority dates for other than provisional patent applications or claims benefits under 35 USC § 119(e) for provisional patent applications, for any and all parent, grandparent, great-grandparent, etc. applications of the Priority Application(s)).

PRIORITY APPLICATIONS

None

If the listings of applications provided above are inconsistent with the listings provided via an ADS, it is the intent of the Applicant to claim priority to each application that appears in the Domestic Benefit/National Stage Information section of the ADS and to each application that appears in the Priority Applications section of this application.

All subject matter of the Priority Applications and of any and all applications related to the Priority Applications by priority claims (directly or indirectly), including any priority claims made and subject matter incorporated by reference therein as of the filing date of the instant application, is incorporated herein by reference to the extent such subject matter is not inconsistent herewith.

TECHNICAL FIELD

This application relates to systems and methods for monitoring and/or tracking airborne material using an unmanned aerial vehicle.

SUMMARY

An unmanned aerial vehicle may be configured to trace airborne materials. In some embodiments, the unmanned aerial vehicle may be configured to mark airborne materials in a plume and/or the plume itself. The unmanned aerial vehicle may eject a tracer material to mark the airborne materials and/or to mark the plume. The tracer material may include macroscopic material, microscopic material, and/or the like. The tracer material may be configured to react and/or interact with the airborne material. The tracer material may be configured to change properties after reacting and/or interacting with the airborne material. The tracer material may be stored in the unmanned aerial vehicle, e.g., in a storage bay, a storage tank, etc., and may be ejected using a nozzle, by opening doors, and/or the like.

The unmanned aerial vehicle may detect a substance of interest in a plume prior to ejecting a tracer material. For example, the unmanned aerial vehicle may include a sensor, which may be configured to detect the substance of interest and/or the plume. The sensor may include a mass spectrometer, an optical spectrometer, an image sensor, and/or the like. The unmanned aerial vehicle may include a laser illuminator in some embodiments, and the sensor may be configured to detect reflections of light from the laser illuminator off of a test substance (e.g., a plume potentially containing the substance of interest). The substance of interest may include a pollutant, an explosive-related compound, a radioactive substance, a biological hazard, a toxic chemical, and/or the like.

The unmanned aerial vehicle may be piloted to a determined location where the tracer material is to be ejected. For example, the unmanned aerial vehicle may be piloted along a gradient of increasing concentration, such as a maximum gradient. Alternatively, or in addition, the unmanned aerial vehicle may be piloted a predetermined distance from the plume while the tracer material is being ejected. The unmanned aerial vehicle may be piloted a predetermined distance from the plume and/or tracer material after the tracer material has been ejected. In some instances, the unmanned aerial vehicle may determine that additional tracer material should be ejected and may eject the additional tracer material into the plume.

The unmanned aerial vehicle may track and/or monitor ejected tracer material (e.g., to determine characteristics of the plume and/or a substance of interest). The unmanned aerial vehicle may be configured to eject the tracer material into a plume and may include a sensor for detecting the ejected tracer material. The unmanned aerial vehicle may monitor and/or track the ejected tracer material based on sensor measurements. The unmanned aerial vehicle may be configured to follow the tracer material and/or the plume as it travels and disperses. The unmanned aerial vehicle may be further configured to compute the characteristics of the plume and/or the substance of interest based on the sensor measurements.

In some embodiments, the unmanned aerial vehicle may include an electromagnetic radiation emitter (e.g., a light emitter) for irradiating the tracer material. The unmanned aerial vehicle may also include a sensor for detecting interactions between the electromagnetic radiation and the tracer material. For example, the sensor may be configured to detect reflections, refractions, scattering, absorption, emission, and/or the like by the tracer material. The sensor may be configured to detect the location of the tracer material, the motion of the tracer material, the concentration of the tracer material, whether the tracer material has reacted with a substance of interest, and/or the like. Alternatively, or in addition, a remote vehicle and/or a stationary remote facility may include a radiation emitter configured to irradiate the tracer material for measurement by the sensor.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

FIG. 6 is a flow diagram of a method for marking airborne material in a plume using an unmanned aerial vehicle.

DETAILED DESCRIPTION OF PREFERRED EMBODIMENTS

Figure 1:
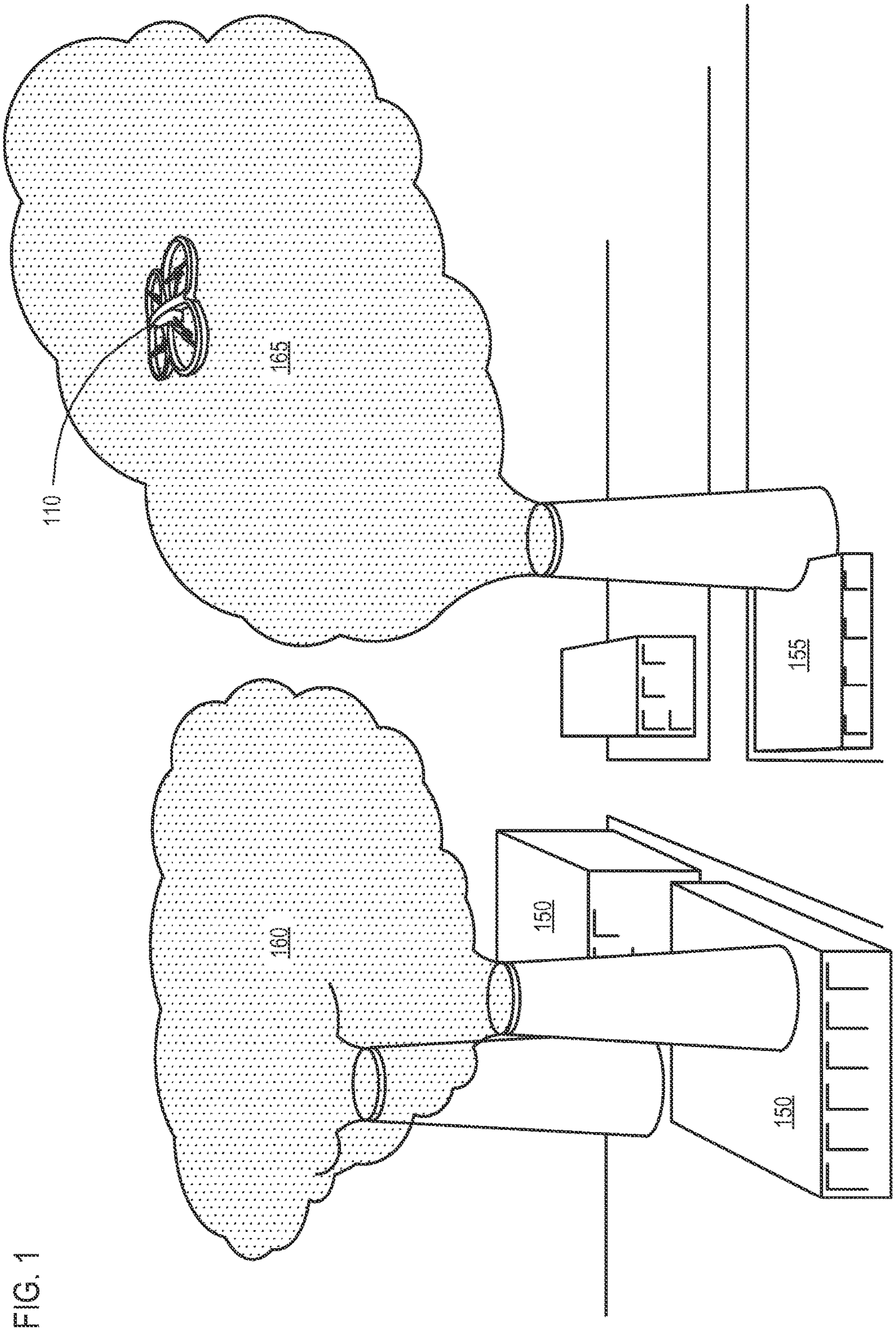
FIG. 1 is a perspective view of an unmanned aerial vehicle configured to mark airborne materials in plumes.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Plumes of airborne material may be emitted into the atmosphere. A source of the plume may be a home, a vehicle, an industrial site, an explosion, a crop field, and/or the like. The airborne material may pollute the atmosphere, nearby land, etc. The airborne material may be traced to determine who is affected by the airborne material in a particular plume and/or to determine the source of airborne material causing harm. However, the plumes of airborne material may be difficult to trace because the plumes may travel long distances and the airborne material may disperse. Accordingly, there is a need for improved techniques for tracking airborne material.

An unmanned aerial vehicle may be configured to mark airborne material so that it can be more easily tracked. The unmanned aerial vehicle may be a remotely piloted aerial vehicle controlled by a remotely located human pilot, an unpiloted aerial vehicle controlled by a locally or remotely located automatic pilot, and/or the like. The unmanned aerial vehicle may include a tracer storage unit configured to hold a tracer material. The unmanned aerial vehicle may also include a tracer dispenser configured to eject the tracer material into the plume. The unmanned aerial vehicle may include a control unit configured to instruct the tracer dispenser to eject the tracer material.

The control unit may include a processor and may decide whether or not the tracer material should be ejected. Alternatively, a communication interface may be configured to receive an indication of whether or not the tracer material should be ejected, and the control unit may instruct the tracer dispenser based on the indication. The control unit may pilot the unmanned aerial vehicle autonomously and/or may pilot the unmanned aerial vehicle based on instructions received from a remote source. Alternatively, or in addition, the remote instructions may bypass the control unit and be provided directly to flight control surfaces and/or the engine(s).

The tracer material may be configured to drift along with the plume. The tracer material may include macroscopic material (e.g., a plurality of macroscopic objects). The macroscopic material may include mini-balloons. The mini-balloons may be marked with tags that uniquely identify each mini-balloon. The tags may include tags readable using radio frequency signals, tags readable optically, and/or the like. The tracer dispenser may be configured to inflate the mini-balloons upon ejection. For example, the unmanned aerial vehicle may store compressed gas for inflating the mini-balloons and/or may compress ambient gases when it inflates the mini-balloons. In some embodiments, the macroscopic material may include radio frequency retroreflectors, optical retroreflectors, chaff, and/or the like.

The tracer material may also, or instead, include a microscopic material. The microscopic material may include a fluorescent material, such as a fluorescent nanocrystal. The microscopic material may include a smart dust, an aerogel, sulfur hexafluoride, a radioactive substance, and/or the like. The tracer material may be configured to react with a substance of interest in the plume, e.g., by a chemical reaction, absorption, etc. The tracer material may change color, change conductivity, change light scattering properties, and/or the like upon reacting with the substance of interest. The tracer material may be configured to sense a substance of interest in the plume. For example, the properties of the tracer material may change in response to the substance of interest without reacting with the substance of interest, e.g., the substance of interest may be adsorbed onto the surface of the tracer material. In some embodiments, the tracer material may be inert and/or may not react or respond to a substance of interest.

The tracer dispenser may be configured based on the material to be released. For example, if the tracer material includes a microscopic material, the tracer dispenser may include a nozzle for ejecting the microscopic material. Alternatively, or in addition, the tracer dispenser may be configured to release many different types of material. The tracer dispenser may include one or more doors for releasing macroscopic and/or microscopic material from a storage area. Similarly, the tracer storage unit may be configured based on the material to be released and may include a storage tank, a storage bay, and/or the like.

The unmanned aerial vehicle may include a sensor configured to detect a substance of interest in the plume. For example, the sensor may detect the plume by detecting the substance of interest. The control unit may be configured to instruct the tracer dispenser to eject the tracer material in response to detecting the substance of interest. In an embodiment, the control unit may instruct the tracer dispenser to eject the tracer material in response to detecting a concentration of the substance of interest above a predetermined threshold. Alternatively, or in addition, the control unit may be configured to determine a gradient of increasing concentration of the substance of interest based on sensor measurements. The control unit may be configured to pilot the unmanned aerial vehicle along the gradient of increasing concentration prior to instructing the tracer dispenser to eject the tracer material. For example, the control unit may pilot the unmanned aerial vehicle to a likely source of the substance of interest, for a predetermined distance, until a predetermined concentration is reached, and/or the like.

The substance of interest may include one or more of a pollutant, an explosive-related compound, a radioactive substance, a biological hazard, a toxic chemical, a compound used for producing illicit drugs (e.g., methamphetamines, etc.), and/or the like. For example, the sensor may be configured to detect a pollutant, such as methane, carbon dioxide, sulfur dioxide, and/or the like. The sensor may be configured to detect an explosive-related compound, such as a reactant, a combustion product, a binder, and/or the like. The sensor may also, or instead, be configured to detect a radioactive substance, a biological hazard, a toxic chemical, and/or the like.

The sensor may include a spectrometer (e.g., an optical spectrometer, a mass spectrometer, etc.). In an embodiment, the sensor may include a laser illuminator. The laser illuminator may emit light at a target substance. The spectrometer may measure a reflection of the light emitted by the laser illuminator off of the target substance. Alternatively, or in addition, the sensor may include a radiation detector, an image sensor, and/or the like. The unmanned aerial vehicle may include a propeller and/or a jet to produce thrust and/or lift, and the sensor may be positioned downstream of the propeller and/or jet. The large volume of air delivered to the sensor by the propeller and/or jet may increase sensitivity to low concentrations of the substance of interest.

The control unit may instruct the tracer dispenser to eject additional tracer material. For example, the control unit may determine that additional tracer material should be ejected. The control unit may determine that additional tracer material should be ejected based on sensor measurements. For example, the sensor measurements may be measurements of the substance of interest and/or measurements of the tracer material, such as the concentration of the substance of interest and/or the tracer material. Alternatively, or in addition, the control unit may instruct the tracer dispenser to eject the additional tracer material in response to a transceiver receiving an indication from a remote source that additional tracer material should be ejected. The remote source may include a remote pilot, a remote server and/or processor, a remote monitoring site, and/or the like. The additional tracer material may include a same material as the previously ejected tracer material and/or a material different from the previously ejected tracer material.

The control unit may be configured to pilot the unmanned aerial vehicle a predetermined distance from the plume while instructing the tracer dispenser to eject the tracer material. For example, the control unit may pilot the unmanned aerial vehicle close enough to the plume to ensure the tracer material enters the plume. The control unit may be configured to pilot the vehicle a predetermined distance from the tracer material after instructing the tracer dispenser to eject the tracer material. For example, the predetermined distance may be selected to prevent disruption to a natural motion of the tracer material and/or the plume. The unmanned aerial vehicle may be a vehicle piloted by the control unit. Alternatively, or in addition, the unmanned aerial vehicle may be remotely piloted by a human or automatic operator, and the control unit may include autopilot functionalities capable of piloting the vehicle during and/or after dispensing the tracer material. In some embodiments, a remotely located automatic pilot may be configured to pilot the vehicle a predetermined distance from the plume and/or tracer material during and/or after dispensing of the tracer material.

The unmanned aerial vehicle may monitor and/or track airborne materials and/or tracer materials in the plume. For example, the unmanned aerial vehicle may include a sensor configured to detect tracer material ejected into the plume. The sensor may be configured to detect any or all of the tracer materials previously discussed. In some embodiments, the control unit may be configured to pilot the unmanned aerial vehicle based upon sensor data concerning the tracer material (e.g., its location, motion, concentration, etc.). In some embodiments, the control unit may be configured to pilot the unmanned aerial vehicle alongside the plume (e.g., matching its motion, maintaining a specified separation from the tracer or plume, etc.), instruct a tracer dispenser to eject tracer material into the plume, and monitor the ejected tracer material based on detections and/or measurements by the sensor.

The control unit may be configured to pilot the unmanned aerial vehicle alongside the plume at a source of the plume. The unmanned aerial vehicle may eject tracer material at the source and/or monitor ejected tracer material from a location near the source. The source may include a chimney, an industrial facility, a nuclear reactor, a crop field, a herd of livestock, and/or the like. In some embodiments, the control unit may pilot the unmanned aerial vehicle along a gradient of increasing concentration prior to ejecting the tracer material, for example, to reach the source.

In some embodiments, the sensor may be configured to directly detect airborne materials of interest. Alternatively, or in addition, the sensor may airborne materials of interest by detecting the tracer material. In some embodiments, the unmanned aerial vehicle may include a first sensor for directly detecting the airborne materials of interest (e.g., to detect a plume containing a substance of interest) and may include a second sensor for detecting tracer material that has interacted with the airborne materials of interest. The first and/or second sensor may be configured to detect a pollutant (e.g., methane, carbon dioxide, sulfur dioxide, etc.), an explosive-related compound, a radioactive substance, a biological hazard, a toxic chemical, and/or the like.

The sensors may include a spectrometer, a radiation detector, an image sensor, and/or the like. In some embodiments, one or both sensors may be positioned downstream of a propeller and/or a jet of the unmanned aerial vehicle. One or both sensors may be configured to measure a differential absorption. One or both sensors may be configured to measure reflections, refractions, scattering, absorptions, emissions, etc. by the tracer and/or airborne material. For example, the unmanned aerial vehicle may include electromagnetic radiation emitter, such as a radio frequency emitter, a light emitter (e.g., a laser), and/or the like to irradiate the tracer and/or airborne material. One or both sensors may measure the electromagnetic radiation after it has interacted with the tracer and/or airborne material.

A remote vehicle (e.g., a remote unmanned aerial vehicle, a ground vehicle, etc.) may emit the electromagnetic radiation at the tracer and/or airborne material. Alternatively, or in addition, a stationary ground facility may emit the electromagnetic radiation at the tracer and/or airborne material. In some embodiments, a remote unmanned aerial vehicle may include a stabilized optic, which may be used to direct the electromagnetic radiation to the tracer and/or airborne material. The remote unmanned aerial vehicle with the stabilized optic may receive the electromagnetic radiation from a remote vehicle, a stationary ground facility, and/or the like. The control unit may position the unmanned aerial vehicle so the sensors can receive the electromagnetic radiation after it has interacted with the tracer and/or airborne material (e.g., so the plume is located between the sensors and the remote light emitter).

The control unit may compute characteristics of the plume, tracer material, and/or airborne material based on the measurements. The control unit may monitor motion of the tracer material, monitor paths of individual tracers, monitor a path of the plume, monitor a dispersion of the plume, monitor a concentration of the tracer material, compute a mass-flux of a substance of interest in the plume, compute a mass-flux of the plume, compute a concentration of a substance of interest in the plume, and/or the like. For example, the control unit may determine locations affected by the plume and/or substance of interest and/or objects with which the plume and/or substance of interest interact. The control unit may monitor reactions of the tracer material with a substance of interest in the plume, such as by monitoring a quantity of tracer material reacted, monitoring a percentage of tracer material reacted, etc.

Embodiments may include various steps, which may be embodied in machine-executable instructions to be executed by a computer system. A computer system includes one or more general-purpose or special-purpose computers (or other electronic devices). The computer system may include hardware components that include specific logic for performing the steps or may include a combination of hardware, software, and/or firmware.

Embodiments may also be provided as a computer program product including a computer-readable medium having stored thereon instructions that may be used to program a computer system or other electronic device to perform the processes described herein. The computer-readable medium may include, but is not limited to: hard drives, floppy diskettes, optical disks, CD ROMs, DVD ROMs, ROMs, RAMs, EPROMs, EEPROMs, magnetic or optical cards, solid-state memory devices, or other types of media/computer-readable media suitable for storing electronic instructions.

Computer systems and the computers in a computer system may be connected via a network. Suitable networks for configuration and/or use as described herein include one or more local area networks, wide area networks, metropolitan area networks, and/or "Internet" or IP networks, such as the World Wide Web, a private Internet, a secure Internet, a value-added network, a virtual private network, an extranet, an intranet, or even standalone machines which communicate with other machines by physical transport of media (a so-called "sneakernet"). In particular, a suitable network may be formed from parts or entireties of two or more other networks, including networks using disparate hardware and network communication technologies.

One suitable network includes a server and several clients; other suitable networks may contain other combinations of servers, clients, and/or peer-to-peer nodes, and a given computer system may function both as a client and as a server. Each network includes at least two computers or computer systems, such as the server and/or clients. A computer system may include a workstation, laptop computer, disconnectable mobile computer, server, mainframe, cluster, so-called "network computer" or "thin client," tablet, smart phone, personal digital assistant or other hand-held computing device, "smart" consumer electronics device or appliance, medical device, or a combination thereof.

The network may include communications or networking software, such as the software available from Novell, Microsoft, Artisoft, and other vendors, and may operate using TCP/IP, SPX, IPX, and other protocols over twisted pair, coaxial, or optical fiber cables, telephone lines, radio waves, satellites, microwave relays, modulated AC power lines, physical media transfer, and/or other data transmission "wires" and/or wireless protocols known to those of skill in the art. The network may encompass smaller networks and/or be connectable to other networks through a gateway or similar mechanism.

Each computer system includes at least a processor and a memory; computer systems may also include various input devices and/or output devices. The processor may include a general purpose device, such as an Intel®, AMD®, or other "off-the-shelf" microprocessor. The processor may include a special purpose processing device, such as an ASIC, SoC, SiP, FPGA, PAL, PLA, FPLA, PLD, or other customized or programmable device. The memory may include static RAM, dynamic RAM, flash memory, one or more flip-flops, ROM, CD-ROM, disk, tape, magnetic, optical, or other computer storage medium. The input device(s) may include a keyboard, mouse, touch screen, light pen, tablet, microphone, sensor, or other hardware with accompanying firmware and/or software. The output device(s) may include a monitor or other display, printer, speech or text synthesizer, switch, signal line, or other hardware with accompanying firmware and/or software.

The computer systems may be capable of using a floppy drive, tape drive, optical drive, magneto-optical drive, or other means to read a storage medium. A suitable storage medium includes a magnetic, optical, or other computer-readable storage device having a specific physical configuration. Suitable storage devices include floppy disks, hard disks, tape, CD-ROMs, DVDs, PROMs, random access memory, flash memory, and other computer system storage devices. The physical configuration represents data and instructions which cause the computer system to operate in a specific and predefined manner as described herein.

Suitable software to assist in implementing the invention is readily provided by those of skill in the pertinent art(s) using the teachings presented here and programming languages and tools, such as Java, Pascal, C++, C, database languages, APIs, SDKs, assembly, firmware, microcode, and/or other languages and tools. Suitable signal formats may be embodied in analog or digital form, with or without error detection and/or correction bits, packet headers, network addresses in a specific format, and/or other supporting data readily provided by those of skill in the pertinent art(s).

Several aspects of the embodiments described will be illustrated as software modules or components. As used herein, a software module or component may include any type of computer instruction or computer executable code located within a memory device. A software module may, for instance, include one or more physical or logical blocks of computer instructions, which may be organized as a routine, program, object, component, data structure, etc., that perform one or more tasks or implement particular abstract data types.

In certain embodiments, a particular software module may include disparate instructions stored in different locations of a memory device, different memory devices, or different computers, which together implement the described functionality of the module. Indeed, a module may include a single instruction or many instructions, and may be distributed over several different code segments, among different programs, and across several memory devices. Some embodiments may be practiced in a distributed computing environment where tasks are performed by a remote processing device linked through a communications network. In a distributed computing environment, software modules may be located in local and/or remote memory storage devices. In addition, data being tied or rendered together in a database record may be resident in the same memory device, or across several memory devices, and may be linked together in fields of a record in a database across a network.

Much of the infrastructure that can be used according to the present invention is already available, such as: general purpose computers; computer programming tools and techniques; computer networks and networking technologies; digital storage media; authentication; access control; and other security tools and techniques provided by public keys, encryption, firewalls, and/or other means.

FIG. 1 is a perspective view of an unmanned aerial vehicle 110 configured to mark airborne materials in plumes 160. For example, one or more sources 150 may emit plumes of airborne material 160. The one or more sources 150 may include factories, power plants, vehicles, crop fields, and/or the like. The unmanned aerial vehicle 110 may be configured to detect a substance of interest in a plume 165 and/or to detect the plume 165 itself. In some embodiments, the unmanned aerial vehicle 110 may initially detect the plume 165 and may then determine whether the plume 165 contains a substance of interest.

The unmanned aerial vehicle 110 may determine a gradient of increasing concentration of the substance of interest and travel up the gradient of increasing concentration to reach a source 155 of the plume 165 and/or to reach a location where the concentration of the substance of interest is above a predetermined threshold. In the illustrated embodiment, the unmanned aerial vehicle 110 includes a sensor (not shown) that requires the unmanned aerial vehicle 110 to be in the plume to detect the substance of interest (e.g., a mass spectrometer, a chemical sensor, etc.). In alternate embodiments, the unmanned aerial vehicle 110 may include a sensor able to detect the substance of interest from near the plume (e.g., an optical spectrometer, an image sensor, etc.).

Figure 2:
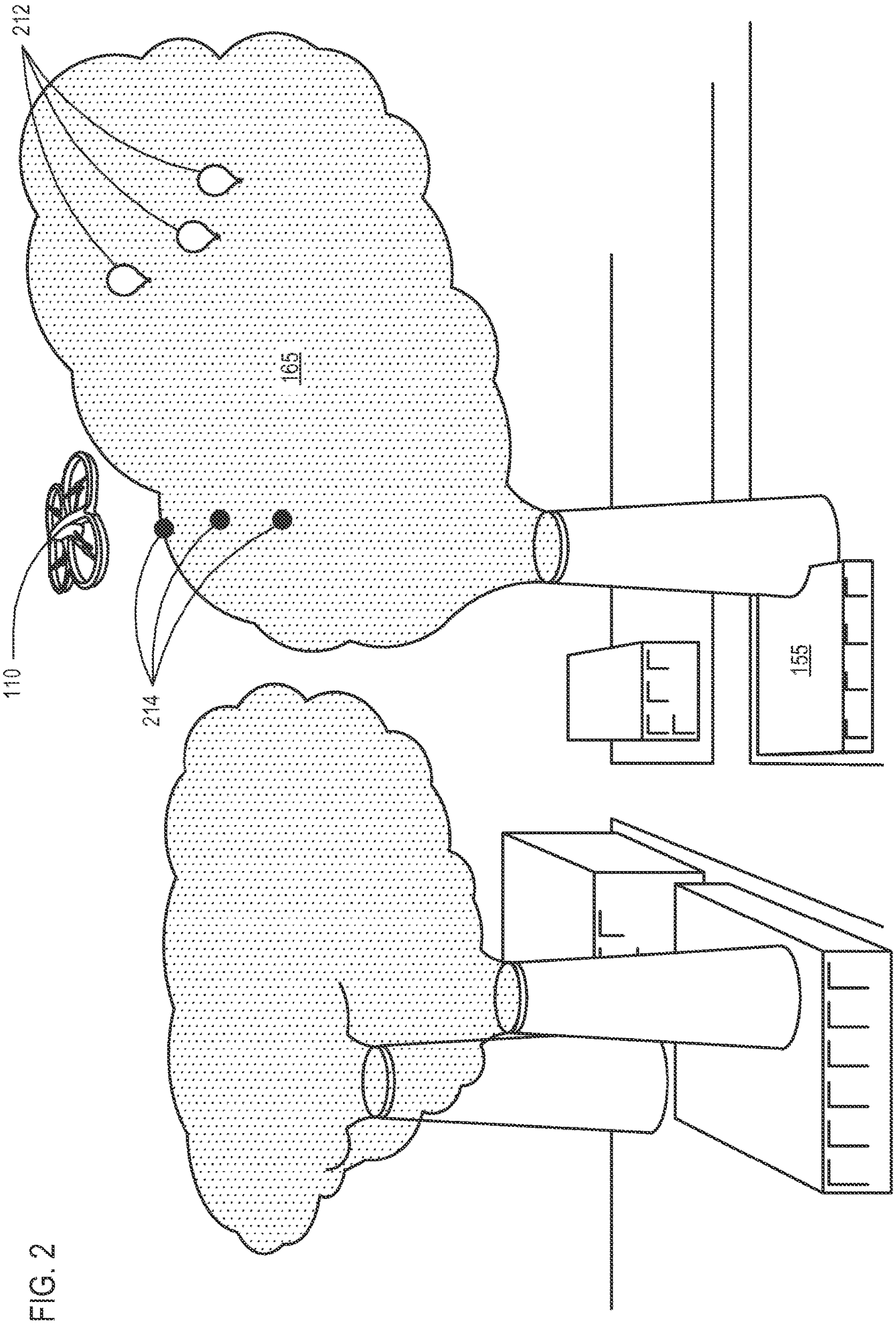
FIG. 2 is a perspective view of an unmanned aerial vehicle that has released tracer materials into a plume of interest.

FIG. 2 is a perspective view of an unmanned aerial vehicle 110 that has released tracer materials 212, 214 into a plume of interest 165. The unmanned aerial vehicle 110 may release the tracer materials 212, 214 into the plume 165 in response to detecting a substance of interest, in response to detecting a concentration of a substance of interest above a predetermined threshold, in response to determining a source of the substance of interest has likely been reached, in response to receiving an indication to dispense the tracer materials 212, 214, and/or the like. For example, the unmanned aerial vehicle 110 may have detected the plume 165, may have determined that the plume 165 included a substance of interest, and may have travelled up the plume 165 to a source. Then, the unmanned aerial vehicle 110 may have positioned itself and dispensed the tracer materials 212, 214 so that the tracer materials 212, 214 entered the plume. After dispensing the tracer materials 212, 214, the unmanned aerial vehicle 110 may fly a predetermined distance from the plume 165, the substance of interest, and/or the tracer materials 212, 214.

The tracer materials 212, 214 may include macroscopic material 212, such as mini-balloons, configured to float in the plume 165 (e.g., the macroscopic material 212 may be configured to be approximately neutrally buoyant in the plume 165). The tracer materials may also include microscopic materials 214 configured to react or interact with the substance of interest or configured to float in the plume 165. In the illustrated embodiment, the unmanned aerial vehicle 110 has released both macroscopic material 212 and microscopic material 214. In alternate embodiments, the unmanned aerial vehicle 110 may only carry macroscopic material 212, may only carry microscopic material 214, and/or may determine that one of the macroscopic material 212 and the microscopic material 214 should be released. For example, the unmanned aerial vehicle 110 may initially release macroscopic material 212 to mark the plume 165. A predetermined distance from the source 155, the unmanned aerial vehicle 110 may also release microscopic material 214 to react and/or interact with the substance of interest (e.g., to determine a concentration of the substance of interest at the predetermined distance). In some embodiments, the tracer materials 212, 214 may be selected based on the substance of interest.

Figure 3:
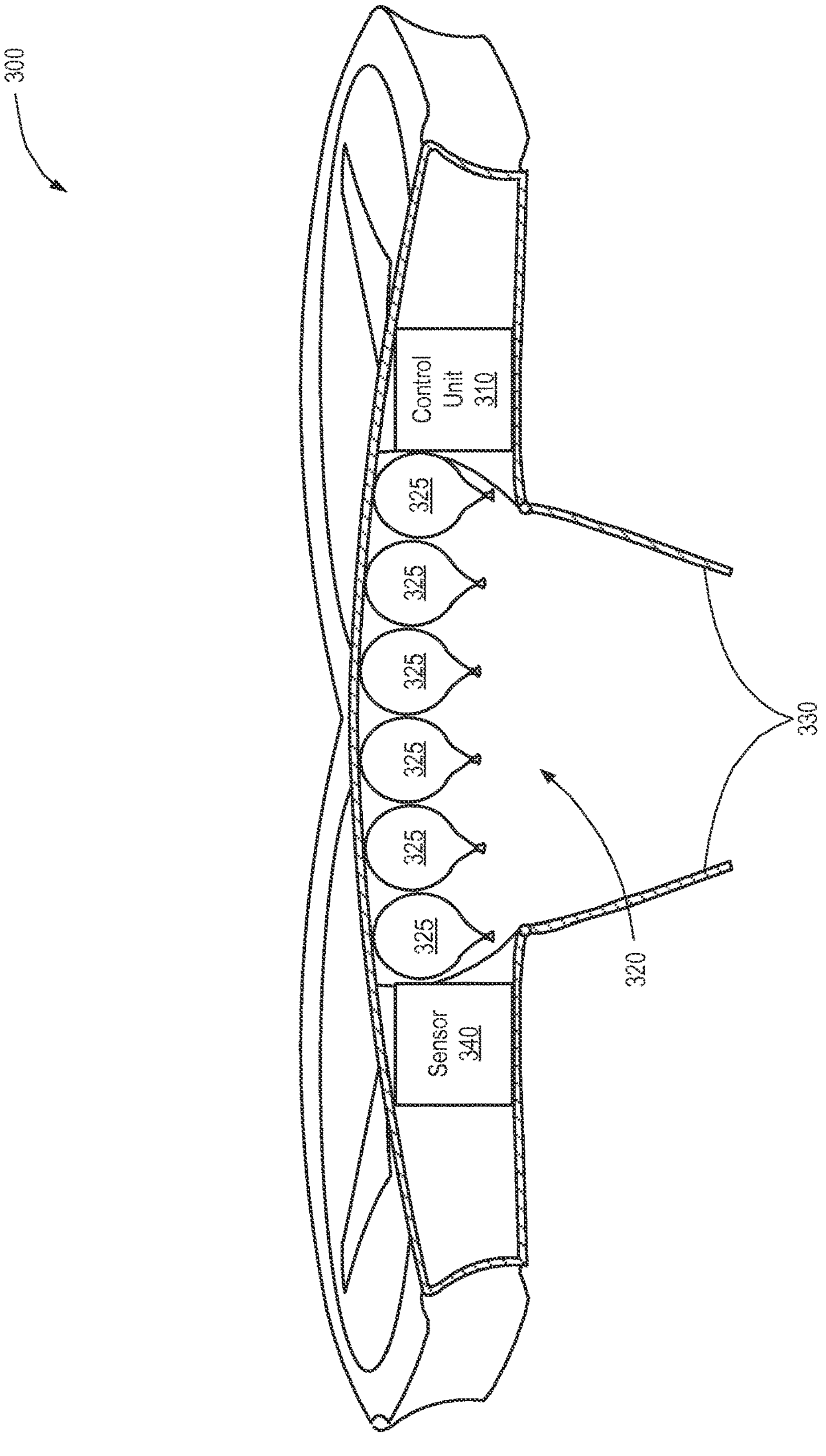
FIG. 3 is a schematic diagram of an unmanned aerial vehicle configured to mark airborne material.

FIG. 3 is a schematic diagram of an unmanned aerial vehicle 300 configured to mark airborne material. The unmanned aerial vehicle 300 may include a control unit 310. The control unit 310 may be configured to instruct a tracer dispenser 330 to eject tracer material. The control unit 310 may also, or instead, be configured to pilot the unmanned aerial vehicle 300. Alternatively, or in addition, the control unit 310 may be configured to receive instructions, and the control unit 310 may instruct the tracer dispenser 330 to eject tracer material and/or may pilot the unmanned aerial vehicle 300 based on the received instructions. For example, the unmanned aerial vehicle 300 may include a transceiver configured to receive instructions from a remote human pilot and/or automatic pilot. The remote human pilot and/or automatic pilot may determine when to eject the tracer material and/or may pilot the unmanned aerial vehicle.

The unmanned aerial vehicle 300 may include a sensor 340. The sensor 340 may be configured to detect a substance of interest and/or a plume. The sensor 340 may be configured to determine a gradient of increasing concentration of a substance of interest. Alternatively, or in addition, the control unit 310 may be able to determine a gradient of increasing concentration of a substance of interest based on a plurality of measurements by the sensor 340. The sensor 340 may include an image sensor, a chemical sensor, a mass spectrometer, an optical spectrometer, and/or the like. The sensor 340 may be configured to detect a substance of interest. For example, the sensor 340 may be designed for detecting a particular substance and/or may be able to detect a dynamically selected substance of interest.

The unmanned aerial vehicle 300 may include a storage area 320. The storage area 320 may be configured to hold tracer material 325 until the unmanned aerial vehicle 300 is ready to dispense the tracer material 325. In the illustrated embodiment, the storage area 320 includes a storage bay which contains a macroscopic material. For example, the storage area 320 may contain previously inflated mini-balloons. In alternate embodiments, the storage area 320 may hold uninflated mini-balloons, which may be inflated before or during dispensing.

The unmanned aerial vehicle 300 may include a tracer dispenser 330 configured to eject the tracer material 325. In the illustrated embodiment, the tracer dispenser 330 may include doors that seal the storage area 320 when closed. The doors may open to release the tracer material 325. The tracer dispenser 330 may be communicatively coupled to the control unit 310, which may control ejection of the tracer material 325 (e.g., opening and closing of the doors). In some embodiments, the control unit 310 may be programmed to pilot the unmanned aerial vehicle 300 a predetermined distance from a plume into which the tracer material 325 will be released. The distance may be predetermined based on the aerodynamic properties of the tracer material 325, and/or the distance may be dynamically determined based on the motion of the tracer material 325 after it is released.

Figure 4:
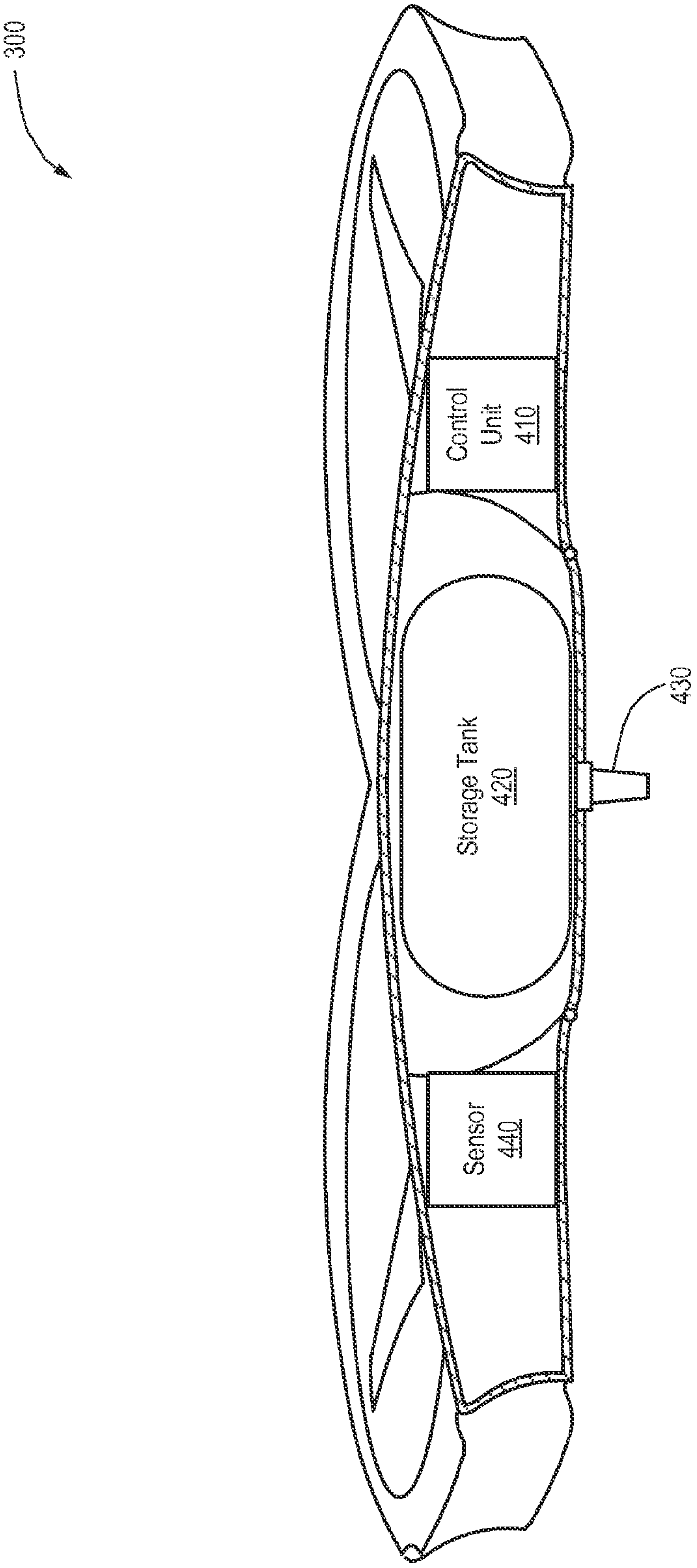
FIG. 4 is a schematic diagram of an unmanned aerial vehicle configured to mark airborne materials.

FIG. 4 is a schematic diagram of an unmanned aerial vehicle 400 configured to mark airborne materials. The unmanned aerial vehicle 400 may be configured to store a microscopic tracer material. For example, the unmanned aerial vehicle 400 may include a storage tank 420 rather than a storage bay. The storage tank 420 may be designed to prevent leaking of or corrosion from the microscopic material. For example, the storage tank 420 may be designed for storage of a particular tracer material and/or may be designed for storage of any of or multiple of a plurality of different tracer materials.

The unmanned aerial vehicle 400 may include a nozzle 430 as a tracer dispenser. The nozzle 430 may be coupled to the storage tank 420 and configured to eject the contents of the storage tank 420 when instructed to do so, for example, by a control unit 410. In an embodiment, the storage tank 420 may store contents under pressure and the nozzle 430 may include a valve configured to receive signals to open or close from the control unit 410. The size of the nozzle 430 (e.g., an orifice diameter) may be selected based on the tracer material to be released. Alternatively, or in addition, the nozzle 430 may be sized for any of or multiple of a plurality of different tracer materials.

The unmanned aerial vehicle 400 may include a sensor 440 similar to the sensor 340. The sensor 440 may be configured to detect a substance of interest. In some embodiments, the sensor 440 and/or the control unit 410 may be configured to determine a gradient of increasing concentration of the substance of interest. Once the substance of interest has been detected by the sensor 440, a concentration of the substance of interest above a predetermined threshold has been detected by the sensor 440, the unmanned aerial vehicle 400 has been piloted up the gradient of increasing concentration, or the like, the control unit 410 may determine that the tracer material should be ejected into the plume. The control unit 410 may pilot the unmanned aerial vehicle 400 a predetermined and/or dynamically determined distance from the plume while the tracer material is ejected. The distance may be selected so that the tracer material enters the plume and remains within it.

Figure 5:
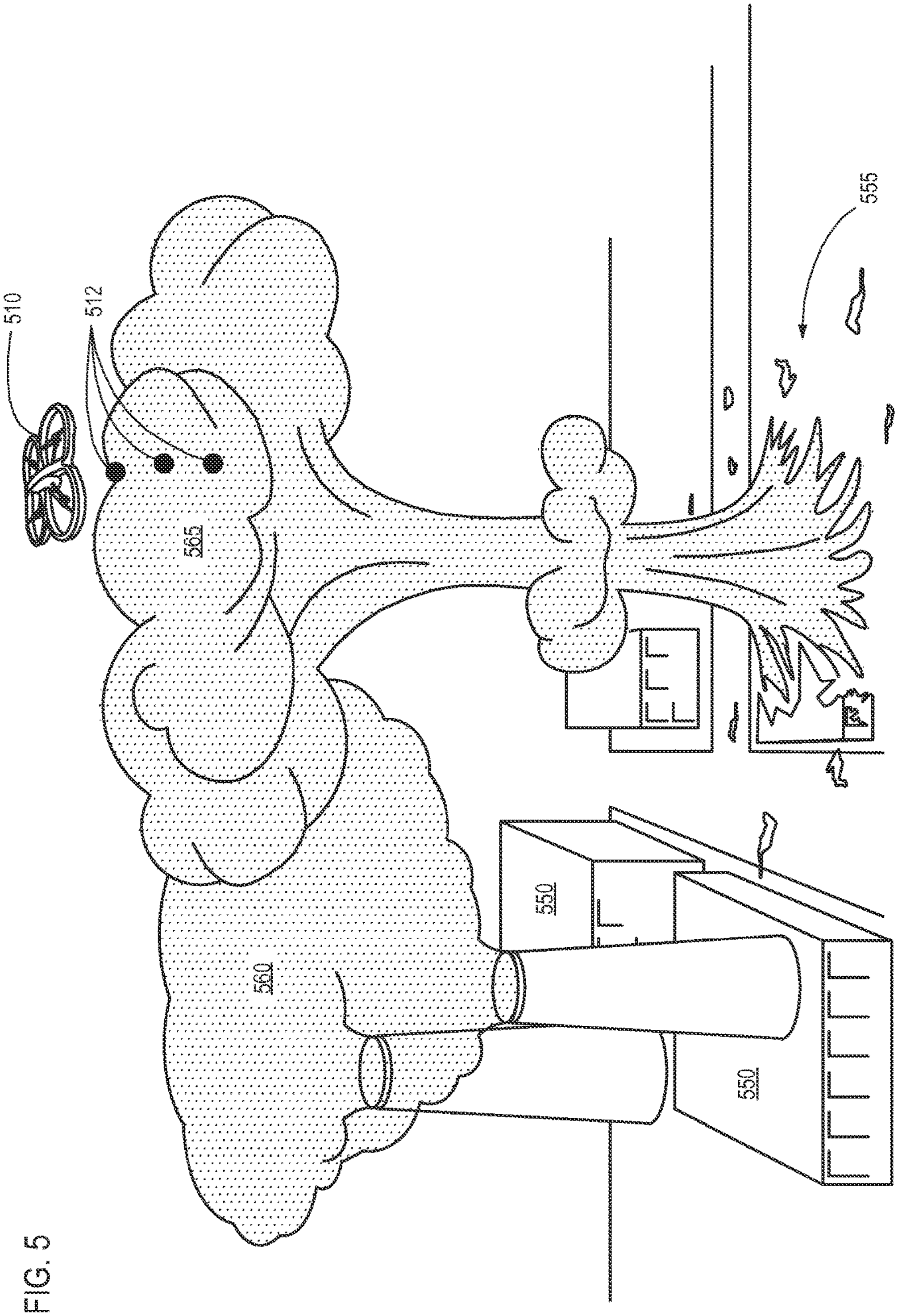
FIG. 5 is a perspective view of an unmanned aerial vehicle configured to mark airborne material in a plume.

FIG. 5 is a perspective view of an unmanned aerial vehicle 510 configured to mark airborne material in a plume 565. In the illustrated embodiment, the plume 565 may be the result of an explosion 555. Accordingly, the plume 565 may include explosive-related compounds, radioactive substances, biological hazards, toxic chemicals, and/or the like. The unmanned aerial vehicle 510 may be able to detect the plume 565 and distinguish it from plumes 560 from other sources 550. For example, the unmanned aerial vehicle 510 may be able to detect the explosive-related compounds, radioactive substances, biological hazards, toxic chemicals, and/or the like to identify the plume 565.

Explosions may be finite sources of plumes and airborne materials rather than continuous sources. For finite sources, the plume 565 may stop being produced before the unmanned aerial vehicle 510 is able to reach the source. Accordingly, the unmanned aerial vehicle 510 may not attempt to climb a gradient of increasing concentration and/or may do so for only a limited amount of time. For a finite plume 565, especially one containing a very hazardous substance of interest, the unmanned aerial vehicle 510 may attempt to eject the tracer material 512 into as much of the plume as possible so that as much as the plume as possible can be traced. For example, the unmanned aerial vehicle 510 may attempt to detect the contours of the plume 565 (e.g., using a sensor) and thereby determine where to eject the tracer material 512.

FIG. 6 is a flow diagram of a method 600 for marking airborne material in a plume using an unmanned aerial vehicle. The method 600 may begin with storing 602 tracer material in an unmanned aerial vehicle. For example, macroscopic tracer material, microscopic tracer material, and/or the like may be stored in the unmanned aerial vehicle. The tracer material may be stored 602 by storing a container holding the tracer material and/or by loading the tracer material directly into the unmanned aerial vehicle.

A substance of interest may be detected 604 in a plume. The substance of interest may be detected 604 by performing measurements using a sensor. The sensor may be configured to detect a particular substance of interest and/or that the substance of interest is of a particular type (e.g., emits radiation, belongs to a particular class of compounds, etc.). Alternatively, the plume itself may be detected, for example, using a sensor. In some embodiments, the unmanned aerial vehicle may be piloted 606 along a gradient of increasing concentration of the substance of interest. For example, the gradient of increasing concentration may be measured and/or computed from measurements. The unmanned aerial vehicle may be piloted to a source, for a predetermined time, until a predetermined concentration of the substance of interest is reached, and/or the like.

Tracer material may be ejected 608 into the plume. The tracer material may be ejected 608 once predetermined criteria have been satisfied. For example, the tracer material may be ejected once the unmanned aerial vehicle has finished piloting up the gradient, once the substance of interest has been detected, and/or the like. The manner of ejecting the tracer material may depend on the particular tracer material to be ejected. For example, in some embodiments, microscopic material may be ejected using a nozzle. Macroscopic and/or microscopic material may be ejected by opening doors enclosing the tracer material. The unmanned aerial vehicle may be piloted a predetermined distance from the plume while the tracer material is being ejected 608. For example, the predetermined distance may be selected to maximize the probability that the ejected tracer material enters and remains in the plume.

After the tracer material has been ejected into the plume, the unmanned aerial vehicle may be piloted 610 a predetermined distance from the plume. For example, the predetermined distance may be selected so that the unmanned aerial vehicle does not disturb the plume, the substance of interest, the tracer material, and/or the like. The position of the unmanned aerial vehicle may also or instead be selected to prevent disruption to the plume, the substance of interest, the tracer material, etc.

In some embodiments, measurements of the plume, the substance of interest, the tracer material, and/or the like may be performed by the unmanned aerial vehicle and/or by a remote monitoring site or vehicle. Based on the measurements, it may be determined 612 that additional tracer material should be ejected. For example, it may be determined that the previously released tracer material has separated from the plume, that the concentration of the substance of interest has changed (e.g., a higher concentration has been detected), that the plume has changed direction or shape, and/or the like. The additional tracer material may then be ejected 614 into the plume. For example, the unmanned aerial vehicle may be piloted a predetermined distance from the plume and/or to a selected location, and the additional tracer material may be ejected 614. The additional tracer material may be the same as or different from the tracer material previously ejected 608. In some embodiments, different tracer materials may be used for different purposes and/or for tracking different airborne materials. The previously ejected tracer material and/or additional tracer material may be selected accordingly. Elements of the method 600 may be rearranged and/or omitted in some embodiments as would be apparent to those of skill in the art. For example, piloting 606 the vehicle along the gradient of increasing concentration, piloting 610 a predetermined distance from the plume, determining 612 additional tracer material should be ejected, ejecting 614 the additional tracer material, and/or other elements may be omitted in some embodiments.

Figure 7:
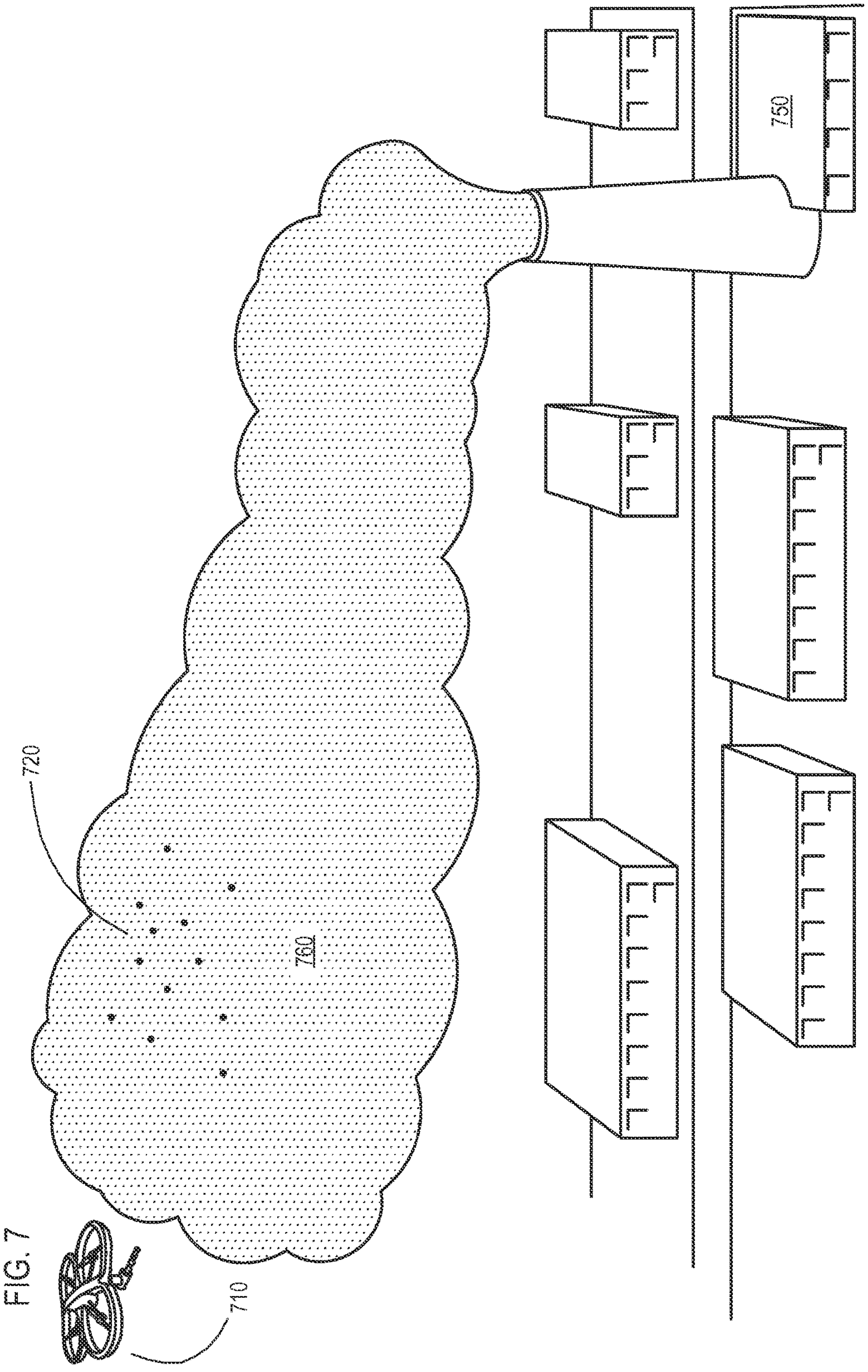
FIG. 7 is a perspective view of an unmanned aerial vehicle configured to monitor and/or track airborne materials in a plume produced by a source.

FIG. 7 is a perspective view of an unmanned aerial vehicle 710 configured to monitor and/or track airborne materials in a plume 760 produced by a source 750. The unmanned aerial vehicle 710 may have ejected a tracer material 720 into the plume 760. The tracer material 720 may be configured to travel with the plume 760. For example, the tracer material 720 may have been ejected near the source 750 and may have traveled away from the source 750 as the portion of the plume 760 into which the tracer material 720 was ejected traveled away from the source 750.

The unmanned aerial vehicle 710 may be configured to follow the tracer material 720 as it travels away from the source 750. The unmanned aerial vehicle 710 may track and/or monitor the tracer material 720 as the unmanned aerial vehicle 710 follows the tracer material 720. In some embodiments, the tracer material 720 may be configured to interact with a substance of interest in the plume 760. The unmanned aerial vehicle 710 may be configured to detect the interaction and may only follow tracer material 720 that has interacted with the substance of interest. Alternatively, or in addition, the tracer material 720 may not interact with the substance of interest, and the unmanned aerial vehicle 710 may assume the tracer material 720 moves along approximately the same path as the plume 760. Based on the tracking and/or monitoring of the tracer material 720, the unmanned aerial vehicle 710 may determine characteristics of the plume 760 and/or a substance of interest in the plume 760. In some embodiments, a remotely located system may determine the characteristics of the plume 760 and/or substance of interest based on measurements reported to the remotely located system by the unmanned aerial vehicle.

Figure 8:
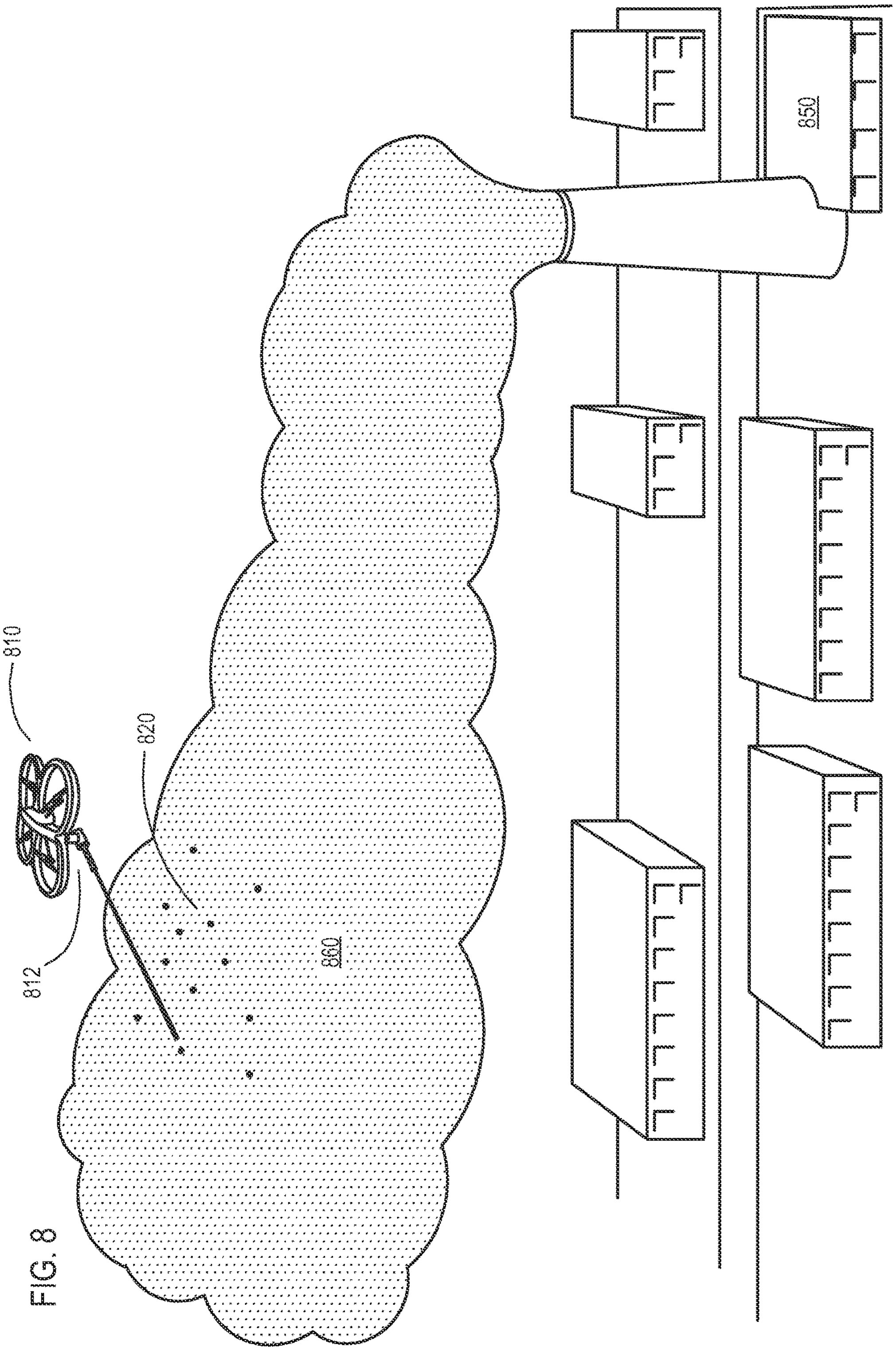
FIG. 8 is a perspective view of an unmanned aerial vehicle configured to irradiate ejected tracer material to monitor and/or track the tracer material.

FIG. 8 is a perspective view of an unmanned aerial vehicle 810 configured to irradiate ejected tracer material 820 to monitor and/or track the tracer material 820. The tracer material 820 may have been ejected by the unmanned aerial vehicle 810 into a plume 860 emitted by a source 850. The unmanned aerial vehicle 810 may include a light emitter 812, such as a laser, for irradiating the tracer material 820. The unmanned aerial vehicle 810 may detect an absorption and/or emission spectrum of the tracer material 820. In an embodiment, the absorption and/or emission spectrum may be used to track the tracer material 820. Alternatively, or in addition, the unmanned aerial vehicle 810 may determine whether the tracer material 820 has reacted with a substance of interest based on the absorption and/or emission spectrum. The unmanned aerial vehicle 810 may determine characteristics of the plume 860 and/or the substance of interest based on measurements of the tracer material 820. For example, if the substance of interest interacts with the tracer material 820, characteristics of the substance of interest may be inferred directly from the measurements of the tracer material 820. If the tracer material 820 does not interact with the substance of interest, the motion of the tracer material 820 may be similar enough to that of the plume 860 and/or the substance of interest to infer characteristics of the plume 860 and/or the substance of interest.

Figure 9:
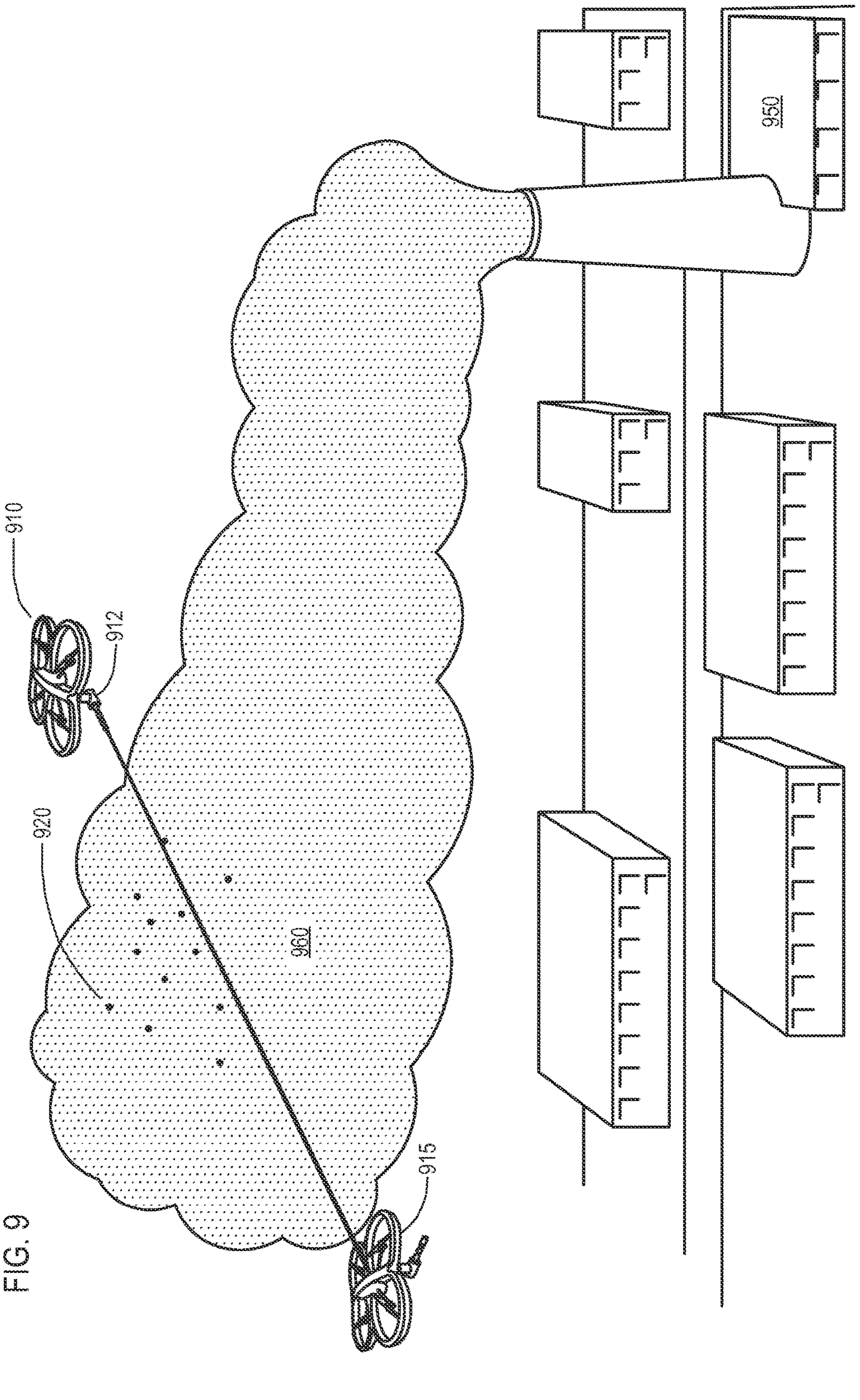
FIG. 9 is a perspective view of a first unmanned aerial vehicle configured to irradiate ejected tracer material for monitoring and/or tracking by a second unmanned aerial vehicle.

FIG. 9 is a perspective view of a first unmanned aerial vehicle 910 configured to irradiate ejected tracer material 920 for monitoring and/or tracking by a second unmanned aerial vehicle 915. The tracer material 920 may have been ejected by the first and/or second unmanned aerial vehicle 910, 915 into a plume 960 emitted by a source 950. The first unmanned aerial vehicle 910 may include a light emitter 912 that it uses to irradiate the tracer material 920 and/or the plume 960. The second unmanned aerial vehicle 915 may position itself so that it receives the emitted light after it has passed through the tracer material 920 and/or the plume 960. Alternatively, or in addition, the first unmanned aerial vehicle 910 may position itself so that the light passes through the plume 960 and/or tracer material 920 before reaching the second unmanned aerial vehicle 915.

The first and second unmanned aerial vehicles 910, 915 may coordinate their positioning with one another and/or may independently determine the optimal location in which to position themselves. In some embodiments, the first and second unmanned aerial vehicles 910, 915 may have a master/slave relationship. Either the first or the second unmanned aerial vehicle 910, 915 may be the master or the slave. In some embodiments, the master may determine a desired position, and the slave may determine its position based on the position of the master. The master may account for the slave's behavior when determining the master's position. Alternatively, or in addition, the master may determine the location of both the master and the slave. In alternate embodiments, one of the unmanned aerial vehicles may be a ground vehicle, stationary ground facility, and/or the like.

Figure 10:
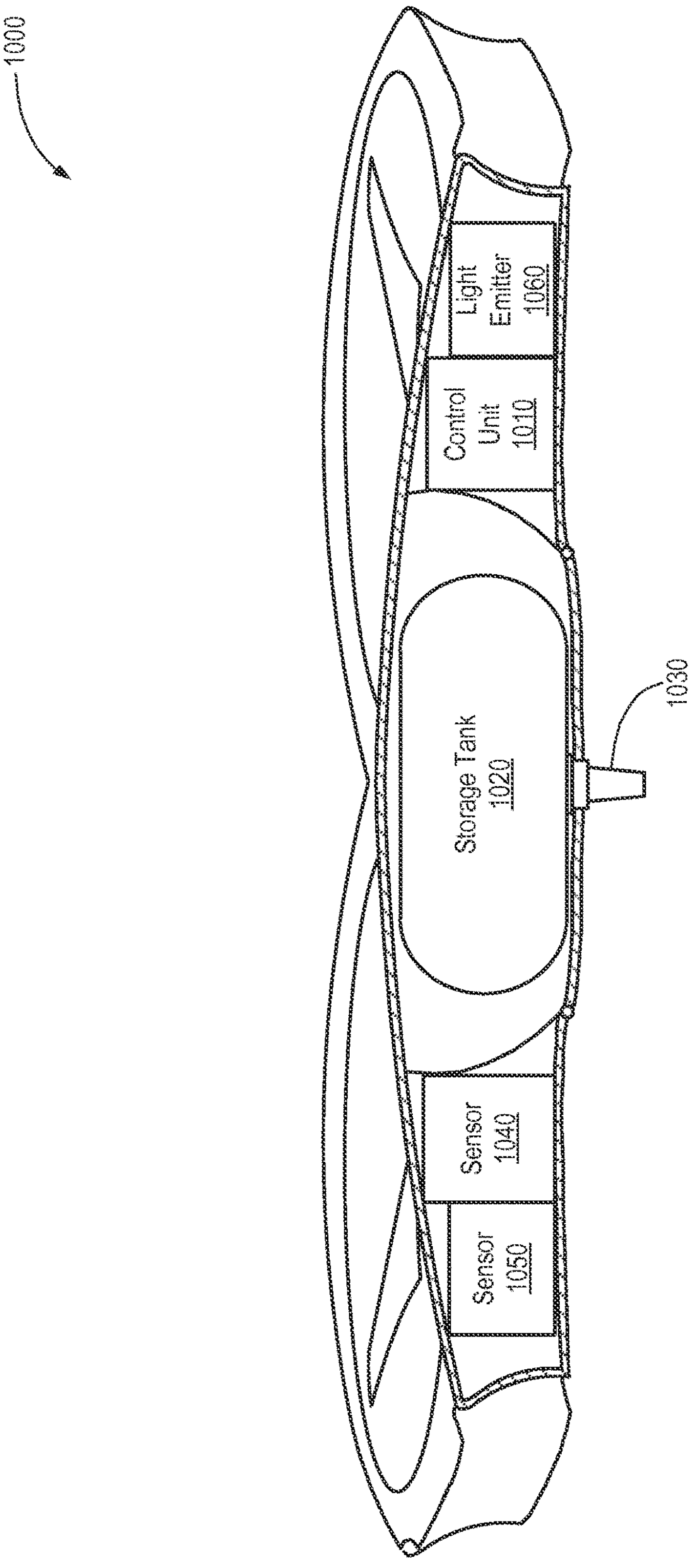
FIG. 10 is a schematic diagram of an unmanned aerial vehicle configured to monitor and/or track airborne material.

FIG. 10 is a schematic diagram of an unmanned aerial vehicle 1000 configured to monitor and/or track airborne material. The unmanned aerial vehicle 1000 may include a control unit 1010, which may be configured to pilot the unmanned aerial vehicle 1000. The unmanned aerial vehicle 1000 may also include a first sensor 1040 configured to detect a substance of interest. In an embodiment, the first sensor 1040 may ingest airborne material and determine whether a substance of interest is present in the ingested material. The control unit 1010 may pilot the unmanned aerial vehicle 1000 based on the measurements by the first sensor 1040. For example, the control unit 1010 and/or the first sensor 1040 may determine a gradient of increasing concentration of the substance of interest based on the measurements by the first sensor 1040, and the control unit 1010 may pilot the unmanned aerial vehicle 1000 up the gradient of increasing concentration.

The unmanned aerial vehicle 1000 may include a storage tank 1020 and a tracer dispenser 1030. The storage tank 1020 may be configured to hold a tracer material, which may be ejected by the tracer dispenser 1030. The control unit 1010 may determine when and where to eject the tracer material. For example, the control unit 1010 may first navigate up the gradient of increasing concentration until a source is reached. The control unit 1010 may instruct the tracer dispenser 1030 to eject the tracer material from the storage tank 1020 once the source has been reached. The control unit 1010 may also determine whether additional ejections of tracer material should occur, for example, after tracking the originally ejected tracer material for a period of time.

The unmanned aerial vehicle 1000 may include a light emitter 1060 and a second sensor 1050. The unmanned aerial vehicle 1000 may irradiate the tracer material and/or the plume using the light emitter 1060. The second sensor 1050 may be configured to measure the interactions of the light emitted by the light emitter 1060 with the tracer material and/or the plume. The second sensor 1050 may be configured to measure reflections, refractions, scatterings, absorptions, emissions, and/or the like by the tracer material and/or the plume. In alternate embodiments, an electromagnetic radiation emitter other than a light emitter may be used to irradiate the tracer material and/or the plume.

The control unit 1010 may be configured to aim the light emitter 1060 (e.g., by aiming the unmanned aerial vehicle 1000 and/or by directly aiming the light emitter 1060) and instruct the light emitter 1060 when to emit light. The control unit 1010 may also be configured to determine characteristics of the tracer material and/or the plume based on measurements by the second sensor 1050. For example, the measurements from the second sensor 1050 may be used by the control unit 1010 to determine locations, concentrations, movements, and/or the like of the tracer material and/or the plume. Alternatively, or in addition, the control unit 1010 may transmit the measurements to a remote system for processing and determining characteristics of the tracer material and/or the plume.

Figure 11:
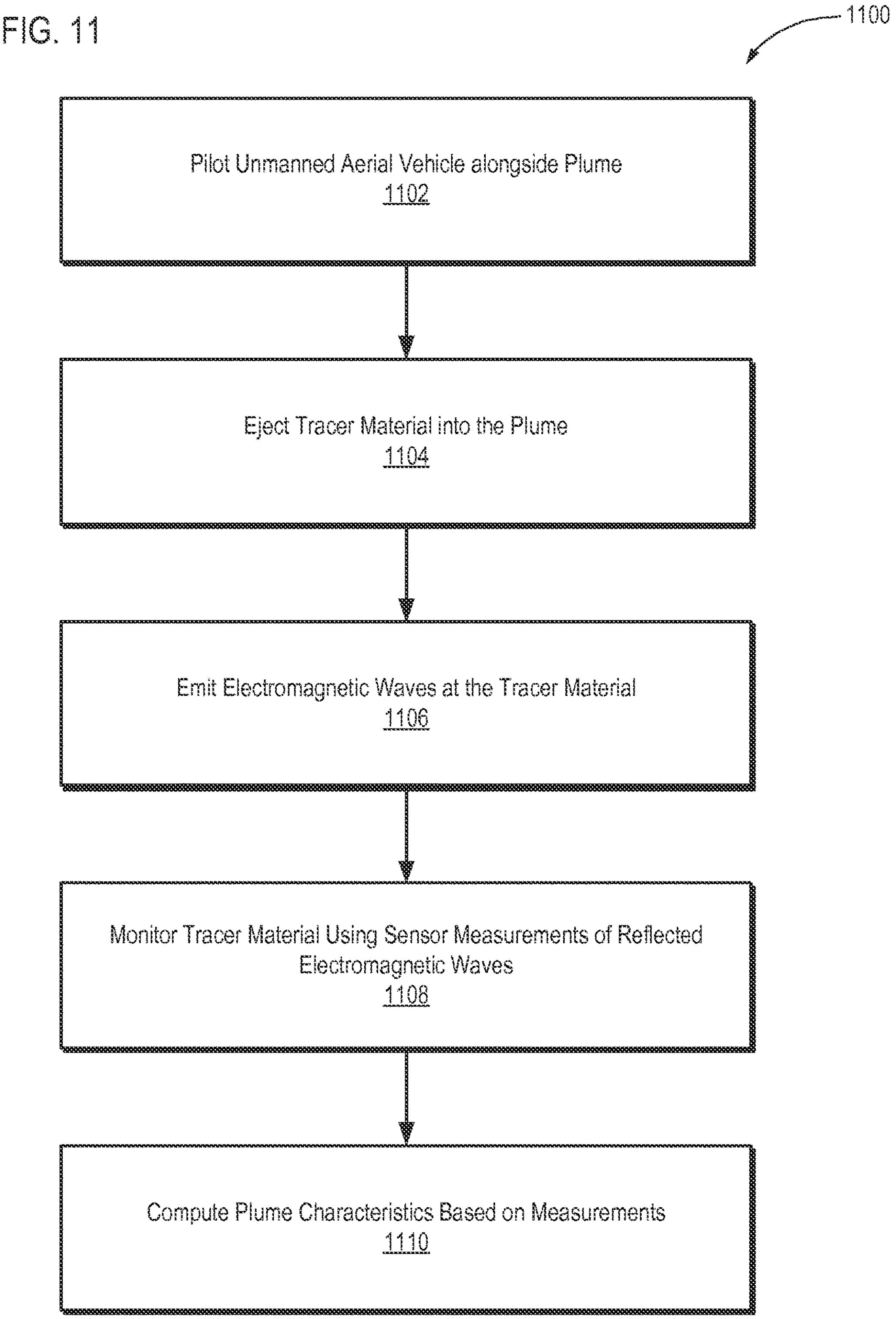
FIG. 11 is a flow diagram of a method for tracking and/or monitoring a plume and/or a substance of interest in the plume.

FIG. 11 is a flow diagram of a method 1100 for tracking and/or monitoring a plume and/or a substance of interest in the plume. The method 1100 may begin with piloting 1102 an unmanned aerial vehicle alongside the plume (e.g., a plume detected by the unmanned aerial vehicle). The piloting 1102 of the unmanned aerial vehicle may include positioning the unmanned aerial vehicle near a source of the plume, piloting the unmanned aerial vehicle up a gradient of increasing concentration, and/or the like. The unmanned aerial vehicle may be positioned in a location where tracer material can be ejected into the plume.

Tracer material may be ejected 1104 into the plume. For example, the unmanned aerial vehicle may store the tracer material internally and may eject 1104 the tracer material from the location to which it was piloted. The location from which the tracer material is ejected 1104 and the rate and/or force used to eject the tracer material may be selected to maximize the amount of tracer material entering the plume.

Electromagnetic radiation may be emitted 1106 at the ejected tracer material. The electromagnetic radiation may include one or more of radio frequency radiation, terahertz radiation, infrared radiation, visible light, ultra violet light, x-rays, gamma rays, and/or the like. The electromagnetic radiation may be selected based on the tracer material and/or a substance of interest. For example, the electromagnetic radiation may be selected to include one or more frequencies where the tracer material and/or the substance of interest is easily identifiable (e.g., frequencies where an absorption and/or emission spectrum is easily identifiable). The unmanned aerial vehicle may be positioned so that the electromagnetic waves can be effectively emitted at the tracer material (e.g., so that there is little distance and/or few or no obstacles between the unmanned aerial vehicle and the tracer material).

The tracer material may be monitored 1108 based on sensor measurements. The sensor measurements may be of electromagnetic radiation reflected, refracted, scattered, absorbed, emitted, etc. by the tracer material. Monitoring the tracer material may include determining whether that tracer material is present, a direction of the tracer material from the unmanned aerial vehicle, movement of the tracer material, a concentration of the tracer material, whether the tracer material has reacted with a substance of interest, and/or the like. Plume characteristics may be computed 1110 based on the measurements. The plume characteristics may include characteristics of a substance of interest in the plume. Computing 1110 the plume characteristics may include determining a location of the tracer material and/or a substance of interest, motion of the tracer material and/or a substance of interest, motion of individual tracers, a concentration of the tracer material and/or a substance of interest, a mass-flux of the tracer material and/or a substance of interest, a location of the plume, a path of the plume, a dispersion of the plume, a mass-flux of the plume, and/or the like. After computing the characteristics, the method 1100 may end or may include continuous and/or repeated piloting 1102, ejecting 1104, emitting 1106, monitoring 1108, and/or computing 1110.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. An unmanned aerial vehicle for monitoring airborne materials in a plume, the vehicle comprising:
- a tracer dispenser that ejects tracer materials;
- a sensor that detects:
  - a substance of interest within a plume, and
  - the ejected tracer material; and
- a control unit in operable communication with the sensor and the tracer, the control unit configured to:
  - pilot the unmanned aerial vehicle alongside the plume,
  - instruct the tracer dispenser to eject the tracer material into the plume based on the sensor detecting a first concentration of the substance of interest greater than a pre-defined threshold within the plume, wherein one or more properties of the ejected tracer material change in response to the substance of interest within the plume,
- monitor the ejected tracer materials for which the one or more properties changed in response to the substance of interest within the plume,
- compute a concentration of the substance of interest in the plume based on information from the sensor detections of the ejected tracer material for which the one or more properties changed in response the substance of interest, and
- evaluate the computed concentration of the substance of interest based on information from the sensor detections of the ejected tracer material in the plume, the evaluation used to characterize the substance of interest and the plume.

2. The vehicle of claim 1, wherein the tracer material comprises radio frequency retroreflectors.

3. The vehicle of claim 1, wherein the tracer material comprises optical retroreflectors.

4. The vehicle of claim 1, wherein the tracer material comprises chaff.

5. The vehicle of claim 1, wherein prior to instructing the tracer dispenser to eject the tracer material, the control unit is configured to:
- determine a gradient of the concentration of the substance of interest in the plume;
- analyze the gradient of the concentration and determine a path of increasing concentration of the substance of interest in the plume; and
- pilot the vehicle along the path of increasing concentration of the substance of interest.

6. The vehicle of claim 1, wherein the control unit is configured to:

determine a gradient of the concentration of the substance of interest in the plume;

analyze the gradient of the concentration and determine a maximum concentration of the substance of interest to identify a source of the plume; and pilot the vehicle alongside the source of the plume.

7. The vehicle of claim 1, further comprising at least one of a propeller and a jet, wherein the sensor is positioned downstream of the at least one of the propeller and the jet.

8. The vehicle of claim 1, wherein the sensor comprises a spectrometer.

9. The vehicle of claim 1, wherein the sensor comprises a radiation detector.

10. The vehicle of claim 1, wherein the sensor comprises an image sensor.

11. The vehicle of claim 1, wherein the sensor is configured to measure a differential absorption.

12. The vehicle of claim 1, further comprising a light emitter, wherein the sensor is configured to measure light received by the light emitter.

13. The vehicle of claim 1, wherein the sensor also measures light coming from a light emitter associated with a second unmanned aerial vehicle, wherein the second unmanned aerial vehicle is positioned at a different location with respect to the unmanned aerial vehicle and the plume so that light from the light emitter that passes through a stabilized optic of the second unmanned aerial vehicle and the plume is received then by the sensor.

14. The vehicle of claim 1, wherein the sensor is configured to detect a pollutant.

15. The vehicle of claim 14, wherein the pollutant is selected from the group consisting of methane, carbon dioxide, and sulfur dioxide.

16. The vehicle of claim 1, wherein the control unit is configured to instruct the tracer dispenser to eject additional tracer material.

17. The vehicle of claim 16, wherein the control unit is configured to determine from sensor measurements that additional tracer material should be ejected, and wherein the control unit is configured to instruct the tracer dispenser to eject the additional tracer material in response to the determination.

18. The vehicle of claim 16, further comprising a transceiver configured to receive an indication that additional tracer material should be ejected, wherein the control unit is configured to instruct the tracer dispenser to eject the additional tracer material in response to the indication.

19. The vehicle of claim 16, wherein the additional tracer material comprises a same material as the ejected tracer material.

20. The vehicle of claim 16, wherein the additional tracer material comprises a different material from the ejected tracer material.

21. A method for monitoring airborne materials in a plume, the method comprising:

piloting an unmanned aerial vehicle alongside a plume;

detecting a substance of interest within the plume;

instructing the tracer dispenser to eject the tracer material into the plume based on the sensor detecting a concentration of the substance of interest greater than a pre-defined threshold within the plume, wherein one or more properties of the ejected tracer material change in response to the substance of interest within the plume;

monitoring the ejected tracer material for which the one or more properties changed in response to the substance of interest within the plume;

computing a concentration of the substance of interest in the plume based on information from the sensor detections of the ejected tracer material for which the one or more properties changed in response to the substance of interest; and evaluating the computed concentration of the substance of interest based on information from the sensor detections of the ejected tracer material in the plume, the evaluation used to characterize the substance of interest and the plume.

22. The method of claim 21, wherein the tracer material comprises radio frequency retroreflectors.

23. The method of claim 21, wherein the tracer material comprises optical retroreflectors.

24. The method of claim 21, wherein the tracer material comprises chaff.

25. The method of claim 21, wherein prior to causing the unmanned aerial vehicle to eject tracer material into the plume, the method comprises:

determining a gradient of the concentration of the substance of interest in the plume;

analyzing the gradient of the concentration and determining a path of increasing concentration of the substance of interest in the plume; and piloting the vehicle along the path of increasing concentration of the substance of interest.

26. The method of claim 21, further comprising:

determining a gradient of the concentration of the substance of interest in the plume;

analyzing the gradient of the concentration and determining a maximum concentration of the substance of interest to identify a source of the plume; and piloting the vehicle alongside the source of the plume.

27. The method of claim 21, wherein the unmanned aerial vehicle comprises at least one of a propeller and a jet, and wherein monitoring the ejected tracer material comprises detecting the tracer material downstream of the at least one of the propeller and the jet.

28. The method of claim 21, wherein monitoring the ejected tracer material comprises monitoring the ejected tracer material with a spectrometer.

29. The method of claim 21, wherein monitoring the ejected tracer material comprises monitoring the ejected tracer material with a radiation detector.

30. The method of claim 21, wherein monitoring the ejected tracer material comprises monitoring the ejected tracer material with an image sensor.

31. The method of claim 21, wherein monitoring the ejected tracer material comprises measuring a differential absorption.

32. The method of claim 21, wherein a stationary ground facility is configured to emit light, and wherein monitoring the ejected tracer material comprises measuring light received from the stationary ground facility.

33. The method of claim 1, wherein the monitoring the ejected tracer material includes measuring light coming from a light emitter associated with a second unmanned aerial vehicle, wherein the second unmanned aerial vehicle is positioned at a different location with respect to the unmanned aerial vehicle and the plume so that light from the light emitter that passes through a stabled optic of the second unmanned aerial vehicle and the plume is received then by the sensor.

34. The method of claim 1, wherein piloting the unmanned aerial vehicle comprises positioning the unmanned aerial vehicle so the plume is located between a remote light emitter and the unmanned aerial vehicle.

35. The method of claim 1, wherein monitoring the ejected tracer material comprises computing a mass-flux of a substance of interest in the plume.

36. The method of claim 1, wherein monitoring the ejected tracer material comprises computing a concentration of a substance of interest in the plume.

37. The method of claim 1, wherein monitoring the ejected tracer material comprises computing a mass-flux of the plume.

38. The method of claim 21, wherein monitoring the ejected tracer material comprises monitoring tracer material selected to interact with a pollutant.

39. The method of claim 38, wherein the pollutant is selected from the group consisting of methane, carbon dioxide, and sulfur dioxide.

40. The method of claim 1, further comprising causing the unmanned aerial vehicle to eject additional tracer material.

41. The method of claim 40, further comprising determining from measurements that additional tracer material should be ejected, wherein causing the unmanned aerial vehicle to eject the additional tracer material comprises causing the unmanned aerial vehicle to eject the additional tracer material in response to the determination.

* * * * *

UNITED STATES PATENT AND TRADEMARK OFFICE
CERTIFICATE OF CORRECTION

PATENT NO. : 10,065,739 B2  
APPLICATION NO. : 14/745992  
DATED : September 4, 2018  
INVENTOR(S) : Paul Duesterhoft et al.

Page 1 of 1

It is certified that error appears in the above-identified patent and that said Letters Patent is hereby corrected as shown below:

In the Claims

Column 18, Claim 33, Line 55: "The method of claim 1," should read --The method of claim 21,--

Column 18, Claim 34, Line 64: "The method of claim 1," should read --The method of claim 21,--

Column 19, Claim 35, Line 1: "The method of claim 1," should read --The method of claim 21,--

Column 19, Claim 36, Line 4: "The method of claim 1," should read --The method of claim 21,--

Column 19, Claim 37, Line 7: "The method of claim 1," should read --The method of claim 21,--

Column 19, Claim 40, Line 16: "The method of claim 1," should read --The method of claim 21,--

Signed and Sealed this  
Twenty-sixth Day of March, 2019

Andrei Iancu  
*Director of the United States Patent and Trademark Office*